United States Patent [19]

Casey et al.

[11] Patent Number: 5,066,764
[45] Date of Patent: Nov. 19, 1991

[54] STERICALLY HINDERED DITERTIARY BUTYL BRIDGED DI(CYCLOHEXYLAMINES)

[75] Inventors: Jeremiah P. Casey, Emmaus; Peter A. Lucas, Allentown; Menas S. Vratsanos, Breinigsville, all of Pa.

[73] Assignee: Air Products and Chemicals, Inc., Allentown, Pa.

[21] Appl. No.: 543,899

[22] Filed: Jun. 26, 1990

[51] Int. Cl.$^5$ ............................................. C08G 59/50
[52] U.S. Cl. ................................... 528/122; 528/407; 528/97; 528/99; 564/451; 564/452; 525/504
[58] Field of Search .................. 528/122, 407, 97, 99; 525/504; 564/451, 452

[56] References Cited

U.S. PATENT DOCUMENTS

| | | | |
|---|---|---|---|
| 3,321,438 | 5/1967 | Brooker et al. | 260/47 |
| 3,351,610 | 11/1967 | Preininger et al. | 260/47 |
| 3,629,181 | 12/1971 | Basel et al. | 260/31.8 E |
| 4,026,858 | 5/1977 | Androus et al. | 528/122 X |
| 4,293,687 | 10/1981 | Weissel et al. | 528/346 |
| 4,324,867 | 4/1982 | Patton et al. | 521/159 |
| 4,554,342 | 11/1985 | Corley | 528/90 |
| 4,946,925 | 8/1990 | Strohmayer et al. | 528/122 |

FOREIGN PATENT DOCUMENTS 907294 3/1954 Fed. Rep. of Germany .

Primary Examiner—Earl Nielsen
Attorney, Agent, or Firm—Russell L. Brewer; James C. Simmons; William F. Marsh

[57] ABSTRACT

This invention relates to ditertiary-butyl substituted bridged di(cyclohexylamines) where the tert-butyl substituent is alpha to the amine group and to polyepoxide formulations incorporating the di(cyclohexylamine). The formula of the diamine is:

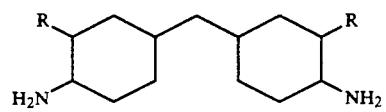

wherein R is tert-butyl.

The di(tertiary butyl)methylene bridged cyclohexylamines have delayed reactivity when incorporated in epoxy resins and they also enhance physical properties in high resilience polyurethane foams.

6 Claims, No Drawings

STERICALLY HINDERED DITERTIARY BUTYL BRIDGED DI(CYCLOHEXYLAMINES)

TECHNICAL FIELD

This invention relates to sterically hindered alkylated bridged di(cyclohexylamines) particularly adapted for curing polyurethanes and epoxy resins and to the resins themselves.

BACKGROUND OF THE INVENTION

Aromatic and aliphatic diamines and alkyl substituted derivatives thereof have been utilized as chain extenders in preparing polyurethanes as well as curatives for epoxy resins. To enhance light stability, the corresponding cyclohexylamine derivatives have been utilized. A variety of substituent groups have been incorporated into the aromatic and cyclohexylamines to alter the reactivity of the amine group for the function intended. Representative patents which show various aromatic diamines and cyclohexyl derivatives thereof for use as intermediates in preparing organic commodities such as polyurethanes and polyepoxide resins are as follows:

German Pat. No. 907,294 discloses the production of 4,4'-diaminodicyclohexyl methanes by hydrogenating 4,4'-diaminodiphenylmethane with hydrogen at high temperatures. Specific derivatives include the 4,4'-diamino-3,3'-dimethyldiphenylmethane; 4,4'-diamino-3,3',5,5'-tetramethyldicyclohexylmethane and 4,4'-diamino-2,2',5,5'-tetramethyldicyclohexylmethane. The compositions are allegedly suited as intermediates for dyes, polymers and textile processing aides.

U.S. Pat. No. 4,324,867 discloses reactive aromatic diamines for preparing polyurethane-polyurea elastomers and are represented by the formula:

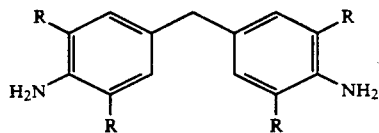

wherein the R groups are hydrogen or an alkyl radical having from 1 to 4 carbon atoms. Representative named diamines include 3,3'-ditertiarybutyl 4,4'-diaminophenylmethane; 3,3'-diethyl-5,5'-diisobutyl-4,4'-diaminophenylmethane; 3,3',5,5'-tetratertbutyl-4,4'-diaminophenylmethane and 3,3'-dimethyl-5,5'-ditertiarybutyl-4,4'-diaminophenylmethane.

U.S. Pat. No. 3,629,181 discloses various cycloaliphatic diamines as curing agents for poly epoxide resins and the diamines include 4,4'-diaminodicyclohexylmethane; 4,4'-methylene-bis-(2-methyl-cyclohexylamine) and others.

U.S. Pat. No. 3,351,610 discloses various epoxy resins compositions utilizing a ditertiary cycloaliphatic amines as the curing agent. Examples include 2,2-bis-(4-dimethylaminocyclohexyl)propane and 4,4'-di-(dimethylamino)-3,3',5,5'-tetramethyldicyclohexylmethane and so forth.

U.S. Pat. No. 3,321,438 discloses various polyamines suited as curing agent for polyepoxide resins. Representative diamines include di(3-methyl-4-amino cyclohexyl)methane and di(4-aminocyclohexyl)methane.

SUMMARY OF THE INVENTION

This invention relates to the ditertiary butyl derivative of bridged dicyclohexylamines into epoxy resins cured with the amine curing agents. The dicyclohexylamine is represented by the structure

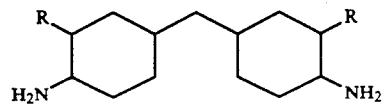

wherein R is tert-butyl.

There are several advantages associated with the composition and the resulting epoxy resins of the present invention and these advantages include:

an ability to permit processing of difficult to handle multifunctional epoxy resins formulations and polyurethane formulations due to enhanced delayed reactivity of the amine curing agents; and an ability to produce more light stable epoxy resins and polyurethanes.

DETAILED DESCRIPTION OF THE INVENTION

One of the problems associated with diamine reactivity in polymer formation, whether it be in polyurethanes or epoxy resins is one of controlled rate. Aromatic diamines are slower reacting than aliphatic diamines and permit processing of polymers under conditions where the aliphatic diamines are unsuited. However, polyurethanes prepared using aromatic diamines are not as light stable as those which are prepared using the aliphatic diamines.

The reactivity of aliphatic diamines in the formation of epoxies, for example, is often controlled through adduction techniques. The aliphatic diamines 1,2-diaminocyclohexane and isophoronediamine may be modified through a Mannich base formation by reaction with phenol and formaldehyde. The aliphatic diamine bis(paraaminocyclohexyl)methane(PACM) has also been utilized in polyurethanes and epoxy resins and its reactivity has been altered by incorporating a methyl group ortho to each amine group. However cure rate retardation is not sufficient in many cases.

The aliphatic diamine 3,3'-ditertiarybutylmethylenedi(cyclohexylamine) (DtBMDCHA), in particular, has been found to satisfy many of the features not heretofore found in aliphatic diamines with respect to low reactivity and physical property alteration in various polymer systems. It is typically prepared by reacting aniline with isobutylene under conditions for forming ortho-tert-butylaniline and then condensing two moles of the ortho-tert-butylaniline with one mole of formaldehyde. The alkylation of aniline by reaction with isobutylene is known and typically is carried out in the presence of an acidic crystalline alumino-silicate. Further detail regarding alkylation is found in U.S. Pat. Nos. 4,740,620 and 4,760,184, both being incorporated by reference.

The condensation reactions of aromatic amines with formaldehyde or acetone to form a methylene or propylidene bridged diamine are also known reactions. Typically, this reaction is carried out at temperatures ranging from 25° to 95° C. at pressures from 15 to 100 psig in the presence of a mineral acid.

Epoxy resin forming systems which can be cured with the bridged aliphatic amines described herein and used in preparing the polyepoxide resin are conventional. They are typically based upon glycidyl polyethers, polyesters and glycidylamines. On reaction with hydrogenated aromatic amines they form the cured polyepoxide resins. Glycidyl ethers of polyhydric phenols typically are formed by reacting epichlorohydrin with polyhydric phenols such as bisphenol A and derivatives thereof. Glycidyl ethers of novolak resins, which are based upon the reaction of an aldehyde with a polyhydric phenol, are also suited. Other representative polyhydric phenols are resorcinol, hydroquinone, 4,4'-(dihydroxydiphenyl)methane, bis(2-hydroxynapthyl)methane, and bis(2-hydroxynapthyl)propane. The glycidyl polyester polyepoxides are based upon the reaction of epichlorohydrin and an aromatic or aliphatic polycarboxylic acid such as phthalic acid or adipic acid. The glycidyl amines formed by the reaction of epichlorohydrin and diamines or aminophenols can also be used as the polyepoxide reactant. Representative diamines that can be reacted with epichlorohydrin include methylenedianiline, bis(paraaminocyclohexy)methane (PACM) and paraaminophenol. Of the above polyepoxide resins, the epoxy resin which is based upon the reaction of epichlorohydrin and bisphenol A is preferred. The polyepoxide resins typically have epoxide equivalent value ranging from 0.1 to 2.5.

It has been found that the use of 3-3'ditertiarybutylmethylene(dicyclohexylamine), when used as the amine curing agent or portion thereof, enhances the resulting physical properties of the polyepoxide resin. Other amines can also be utilized in combination with 3-3'ditertiarybutylmethylenedi(cyclohexylamine) and these include aliphatic amines such as methylcyclohexanediamine, diethylenetriamine, propylenediamine, ethylene diamine, triethylenetetramine, and cycloaliphatic amines such as N-cyclohexyl-1,3-propanediamine, and piperazine.

The level of amine curing agent based upon the moles of polyepoxide resin is conventional and ranges from about 0.4 to 0.6 molar equivalents amine per equivalent epoxide group. Temperatures, pressures, and other conditions suited for curing epoxy systems are conventional and range from 0° to 200° C. and from 0 to 150 psig.

Polyurethanes, whether rigid foams or resilient foams, are formed by reacting a polyisocyanate with a compound having active hydrogen atom, typically a long-chain diol. Crosslinking is achieved by reaction with a short-chain diol or with various combinations of short-chain diol and aliphatic diamine crosslinkers. Representative polyisocyanates include aliphatic diisocyanates such as bis(4-isocyanatocyclohexyl)methane and alkyl-substituted derivatives thereof, toluenediisocyanate, methylenediphenyldiisocyante, paraphenylenediisocyanate, isophoronediisocyanate, and cyclohexanediisocyanate.

Representative diols suited for reaction with the polyisocyanates include polyalkylene ethers or polyester diols. Polyether polyols are typically formed by condensing an alkylene oxide with a diol e.g., the alkyl ethylene and propylene oxide addition products of ethylene gylcol, propylene glycol, butane glycol and hexane glycol. A preferred polyol is poly(tetramethyleneglycol). These typically will have a molecular weight ranging from about 250–10,000. Short-chain diols can be used as crosslinking agents and these include ethylene glycol, propylene glycol, butane diol and others.

For general information regarding polyurethane foam production, reference is made to copending U.S. patent application having Ser. No. 07/499,116 and a filing date of Mar. 26, 1990; the application is incorporated by reference.

The following examples are provided to illustrate the preferred embodiments of the events and are not intended to restrict the scope thereof.

EXAMPLE 1

Preparation of 3,3'-Ditertiarybutylmethylenedianiline

To a 15 gallon and glass stainless steel reactor equipped with an agitator were charged orthotertiarybutylaniline (12.81 kg, 86.0 moles), the orthotertiarybutyl being obtained by the alkylation of aniline with isobutylene followed by fractional distillation of orthotertiarybutylaniline from the reaction product of unreacted aniline, N-tertiarybutylaniline and paratertiarybutylaniline and dionized water. Hydrochloric acid, 8.68 kg of 37% concentrated acid, diluted 2:1 with deionized water, (4.3 kg H$_2$O previously cooled to 25° C.) was then introduced at 150 cc/min into vigorously stirred (1325 rpm) reaction mixture. The temperature was maintained at 25° to 30° C. by the use of appropriately chilled coolant in the reactor coils.

Initially a white salt formed which disappeared over time and the reaction mixture cleared forming a purple solution. Additional deionized water was introduced to the reactor as follows; 2 liter for rinsing the acid reservoir, and 1.5 liter for reducing splashing caused by an upper impeller on the agitator.

The reaction mixture was chilled to approximately 5° C. and formalin (43.0 moles of 36–38% wt % material, previously assayed by the sodium sulfite method) was introduced at a 50 cc/min rate. During the formalin addition, the temperature was maintained between 5° and 12° C. Some foaming was observed during the formalin addition and the mixture became yellowish, then lime green. The temperature was allowed to rise to 20° C. over 30 min. Steam was introduced into the reactor coils and the reactor mixture was heated to 70° C. and maintained between 70° and 80° C. for 90 to 120 minutes. The color of the reaction mixture changed from light green to yellow then to dark yellow. Small samples (approximately 4 cc) were taken during the warm-up and heating period. These were immediately neutralized with aqueous NaOH in the presence of tetrahydrofuran (THF) and then analyzed by GC to monitor reaction progress. After the reaction at elevated temperature was complete, the reactor was cooled down rapidly within 40 to 50 minutes to 25° C.

Approximately one-half of the reaction mixture was withdrawn into a holding vessel. The remaining half was neutralized by adding, with stirring, 12 liters of tetrahydrofuran (spectral grade, containing no inhibitor) and then 6 liters of 50% sodium hydroxide. Stirring was continued for 5–10 minutes. During neutralization the temperature rose to 45°–55° C. The stirring was stopped and the layers were allowed to separate. The bottom layer was withdrawn. The interface layer was efficiently separated using a 4 liter separatory funnel.

The THF extract was withdrawn and stored in a 5 gallon container as the neutralization process was repeated on the other half of the reaction mixture.

Major components excluding THF solvent were:

| Component | GC FID Area % |
| --- | --- |
| o-t-butylaniline | 9.5 |
| p-t-butylaniline | 0.5 |
| di-t-butylmethylenedianiline (DtBMDA) | 71.6 |
| tri-t-butyldimethylenetrianiline | 17.0 |

The THF extract of the product from each batch was concentrated in a 22 liter round bottom distillation flask by continuous stripping of the solvent. The remaining solvent and water were removed by distillation at reduced pressure. The unreacted starting material and a small amount of the DtBMDA product were removed in a forecut by continuous increase in vacuum and temperature to 205°-210° C. and 0.2-0.4 mm Hg. The recovered mixture of product and heavies was transferred to a final distillation in a modified 2" Pope Still operated under the following conditions:

Still pressure: 0.05-0.15 mm Hg
Overhead temperature: 180°-195° C.
Still temperature: 290° C.
Overhead/Bottoms ratio: 2.3-2.7
Feed rate: 8-12 cc/min The DtBMDA recovered was >97% pure with <0.10% lighter material and <3% of tritertiarybutyl-dimethylenetrianiline. Recrystallization from hexane improved purity to 99.3% 3,3'-ditertiarybutylmethylenedianiline), m.p. 82.5°-84° C.

EXAMPLE 2

Preparation of 3,3'-Ditertiarybutylmethylenedi(cyclohexylamine) (DtBMDCHA)

A 466 g (1.5 mole) portion of the 3,3'-ditertiarybutyl-methylenedianiline (DtBMDA) from Example 1 was dissolved in 932 ml tetrahydrofuran (THF) and placed in a 2 liter autoclave. Then 23.3 g 5% Rh on alumina catalyst was added followed by 2.3 g anhydrous lithium hydroxide base promoter. The reactor was sealed, purged three times with nitrogen and then twice with hydrogen before being pressurized with hydrogen, to 3200 psig. The reaction mixture was brought to 175°-180° C. with 750 rpm sealed stirrer agitation and held at that temperature during the reduction. Reactor pressure was allowed to drop to no lower than 2500 psig before being recharged to 3200 psig until slightly greater than stoichiometric hydrogen consumption had occurred (1 hour). The reaction mixture was cooled, vented, and purged with nitrogen. The crude reaction solution was removed from the autoclave, filtered free of catalyst, and analyzed by capillary chromatography. Product diamine (DtBMDCHA) isomers comprised 93.8% of the reaction crudes as analyzed by capillary flame ionization detection.

EXAMPLE 3

Preparation of 3,3'-Ditertiarybutylmethylenedi(cyclohexylamine)(DtBMDCHA)

The procedure of Example 2 was repeated except an alternative catalyst was used. A 466 g (1.5 moles) DtBMDA sample was dissolved in 932 ml THF and placed in the autoclave. Then, 23.3 g of 5% Ru on alumina catalyst was added followed by 2.3 g anhydrous LiOH base promoter. The reactor was purged thrice with nitrogen, thrice with hydrogen and then vented to atmospheric pressure before hydrogen pressurization to 3000 psi. The stirred reaction mass was brought to 175°-180° C. Hydrogen uptake rate was monitored and reactor pressure was maintained between 3200 and 2750 psi. When a slightly greater amount of hydrogen uptake required for reaction was reached (0.6 hours) the reactor was cooled, vented and purged. Crude DtBMDCHA product was 94.5%. Isomer distribution.

With two chiral centers in each ring the potential isomers in methylenedi(cyclohexylamine) (MDCHA) are cis/cis, cis/trans, trans/cis and trans/trans. Due to the plane of symmetry in MDCHA the cis/trans and trans/cis isomers are equivalent, resulting in three isomers. In DtBMDCHA there are three chiral centers in each ring, and no plane of symmetry in the molecule. Within each ring the isomer combinations for the 1,2 and 4 position substituents are again four in number (c/c c/t t/c and t/t). Combining the rings equivalently about the methylene bridge leads to a factorial 16 isomers possible in DtBMDCHA. In the hydrogenation reactions cited above there are nine or so resolved peaks by capillary chromatography. Isomer distribution varied little as a function of run conditions such as catalyst, temperature, and time. For runs 1 and 2 the 6 major resolved isomer peaks, normalized to 100% DtBMDCHA composition, varied as given below:

| Isomer peak | pk1 | pk2 | pk3/4 | pk5 | pk6 |
| --- | --- | --- | --- | --- | --- |
| Run 1 - Rh | 20.4 | 35.1 | 27.8 | 9.2 | 7.4 |
| Run 2 - Ru | 17.3 | 36.7 | 28.4 | 13.6 | 4.0 |

The crude DtBMDCHA was distilled through a 10" Vigreaux column from a 2 L round bottom flask. The product aliphatic diamine was collected at 205°-210° C. under 55-60 microns of Hg pressure. Using a 1"×12" packed column (0.16" stainless steel Propak) the aliphatic diamine isomer mixture was distilled at 214°-216° C. at 2 mm of Hg and showed negligible isomer separation at 1:1 reflux ratio.

EXAMPLE 4

Epoxy Resin Preparation with DtBMDCHA and Comparative Diamines

The instrument used to measure and predict reaction time in epoxy resin/amine curing formulations was a Sunshine ® Gel Time Meter. The principle of operation is based on a circuit disconnect once a rotating glass rod reaches a specific torque. This torque is characteristic of a torsion spring of constant dimensions connected between the rod and the instrument. The rod is immersed in the resin/curing agent formulation held in a test tube and the test tube suspended in a constant temperature bath.

Three run formulations were prepared to determine reactivity profile: Run 1-The first formulation was prepared by charging 100 parts by weight of the diglycidyl ether of Bisphenol A having an epoxide equivalent weight of 187 were mixed with 28.2 parts by weight of a commercial curing agent, methylenedi(cyclohexylamine) (PACM), having an amine hydrogen equivalent weight (AHEW) of 52.5 to a glass container. The mixture was stirred at room temperature (22° C.) until homogeneous but no longer than five (5) minutes. A portion of this mixture (10 g) was placed in the test tube used for the gel meter described above. The gel timer glass rod was placed into the mixture and the test tube secured in a water bath preheated to 60° C. The glass rod was attached to the instrument and aligned so the rotating rod would not touch the sides of the test tube. The gel timer was turned on and allowed to run until a gel time was registered.

Run 2—DMMCHDA

A second formulation, was prepared and tested in a similar manner to Run 1, substituting 32.0 parts by weight of 3,3'-dimethylmethylenedi(cyclohexylamine) (AHEW of 59.5).

Run 3—DtBMDCHA

A third formulation, was prepared and tested in a similar manner to Run 1, substituting 43.3 parts by weight of 3,3'-ditertiarybutylmethylenedi(cyclohexylamine) (AHEW 80.5).

The resultant gel times at 60° C. were:

| Run 1 | Run 2 | Run 3 |
|---|---|---|
| PACM | DMMCHDA | DtBMDCHA |
| 23.2 minutes | 51.7 minutes | 137 minutes |

From the above the delayed reactivity of the DtBMDCHA, the most sterically hindered of the three candidate diamines, is demonstrated.

EXAMPLE 5

Epoxy Exotherm Profiles

Exotherm profiles 4, 5 & 6 of the formulation of Example 1 were carried out and observed using a differential scanning calorimeter (DSC). Curatives for Runs 4, 5 and 6 were identical in composition to curatives in runs 1, 2 and 3 respectively. After each was mixed, it was immediately weighed into a DSC sample pan on an analytical balance and placed in the DSC cell of a DuPont 9900 thermal analyzer. The cell was preprogrammed to increase in temperature from 23° C. to 250° C. at a rate of 10° C./minute. Analysis of the resulting exotherms for each formulation indicates a shift in the location of the peak exotherm for the slower reactivity formulations.

| DSC Reactivity Profile | | | |
|---|---|---|---|
| | Run 4 | Run 5 | Run 6 |
| Curative | PACM | DMMCHDA | DtBMDCHA |
| Onset Temperature, °C. | 88 | 91 | 104 |
| Peak Temperature, °C. | 113 | 124 | 144 |
| ΔH Joules/g | 413 | 304 | 158 |

Again the delayed reactivity of the most sterically hindered aliphatic diamine is demonstrated. The enthalpy of reaction observed for DtBMDCHA, 158 Joules/g, suggests each of the two amine groups is reacting but once with epoxide as opposed to the normal two fold reactivity of each amine in Runs 4 and 5, which have twice the reaction exotherm.

EXAMPLE 6

Epoxy Resin Formulation

To demonstrate the property performance of the compositions of this invention against the prior art, composites/runs 7, 8 and 9 were prepared. Their composition and mix procedure were identical to those of Runs 1), 2) and 3). In addition, sample 10), was prepared using 100 parts by weight of commercial epoxy resin, DEN 438, the polyglycidyl ether of a 3.6 functional phenol-formaldehyde novolak resin having an epoxide equivalent weight of 180 and 43.4 parts by weight of 3,3'-diteritarybutylmethylenedi(cyclohexylamine). Unlike composites 7, 8, 9, in composite/run 10 both the epoxy novolak resin and curing agent were preheated to 80° C. prior to mixing to reduce the viscosity of the epoxy novolak and facilitate mixing.

Each sample was degassed prior to pouring ⅛" thick castings. The castings were gelled and post cured according to the schedule in Table 1. Glass transition temperatures (Tg) were run on the cured castings to determine the extent of cure. A differential scanning calorimeter was used, programmed with a 10° C./minute rate of increase from 23° C. to 250° C. Upon completion of the scan, the sample was cooled to 23° C. in the DSC cell using a dry ice cold finger and a second scan was run under identical conditions. The Tg for each sample is reported from the second scan:

| | Cure and Glass Transitions | | | |
|---|---|---|---|---|
| | Epoxy Composition | | | |
| | Run 7 | Run 8 | Run 9 | Run 10 |
| Amine Curative | PACM | DMMDCHA | DtBMDCHA | DtBMDCHA |
| Cure Schedule | 2 h @ 80° C. | 2 h @ 80° C. | 2 h @ 80° C. | 2 h @ 80° C. |
| | +2 h @ 150° C. | +2 h @ 150° C. | +3 h @ 150° C. | +3 h @ 150° C. |
| | +2 h @ 200° C. | +2 h @ 200° C. | +2 h @ 200° C. | |
| Tg (°C.) | 157 | 161 | 115 | 136 |

Other physical properties were examined using coupons from these same ⅛" thick castings for runs 7-9 to compare equivalent formulations. Those results were as follows:

| | Epoxy Composition | | |
|---|---|---|---|
| | Run 7 | Run 8 | Run 9 |
| Amine Curative | PACM | DMMDCHA | DtBMDCHA |
| Flexural Strength, psi | 23900 | 21400 | 25150 |
| Flexural Modulus, psi × $10^5$ | 5.11 | 5.15 | 5.60 |
| Tensile Strength, psi | 10410 | 10080 | 5160 |
| Tensile Modulus, psi × $10^5$ | 3.25 | 3.53 | 5.99 |
| Tensile Elongation, % | 5.47 | 3.80 | 1.39 |

Use of the crosslinking epoxide resin in run 10 enhances the thermal stability of the resultant epoxy formed from the slow reacting diamine. In runs 7-9 lower tensile strength and much lower elongation demonstrate the difference in aliphatic diamine reactivity for DtBMDCHA versus the other two less sterically hindered primary amines. It again appears full crosslinking is inhibited or substantially inhibited under these conditions with the use of DtBMDCHA.

EXAMPLE 6

Epoxy Resin Reactants

In a separate test to that of Example 5, the delayed reactivity of DtBMDCHA was again compared to that of PACM and DMMDCHA by reaction of the DEN-438 Novolak epoxide resin with an aliphatic diamine considering both two and four amine reactive sites per aliphatic diamine. The components were admixed at 80° C.; the mixed formulations were separately subjected to gel time measurement and cured 2 hours @ 80° C. and then 3 hours @ 150° C. before Tg values were measured:

| Aliphatic Diamine/Sites | ALIPHATIC DIAMINE Diamine/DEN-438 (pph) | Gel Time (min) | Tg (°C.) |
|---|---|---|---|
| MDCHA/2 | 59.1 | 6.1 | 120 |
| DMMDCHA/2 | 67.0 | 10.5 | 121 |
| DtBMDCHA/2 | 90.6 | 48.6 | 45 |
| MDCHA/4 | 29.6 | 4.7 | 189 |
| DMMDCHA/4 | 33.5 | 11.0 | 190 |
| DtBMDCHA/4 | 45.3 | 42.1 | 122 |

The reactivity of the less hindered aliphatic diamines is too fast to allow processing; set-up in the range of 4-11 minutes defies workability for the epoxy mixture; only the sterically hindered aliphatic diamine DtBMDCHA is sufficiently slow to allow processing.

EXAMPLE 7

Polyurethane Formulation

A set of physical properties was measured from a set of hand-mix foam pads for a control and DtBMDCHA-modified formulation. The control is a high water, high resiliency formulation currently used commercially to produce automotive seating foam. Two control pads and three DtBMDCHA-modified pads were tested.

| Control Formulation | DtBMDCHA-modified Formulation |
|---|---|
| 85 parts Multranol 9143 | 85 parts Multranol 9143 |
| 15 parts Multranol 9151 | 15 parts Multranol 9151 |
| 1.5 parts DEOA | 1.5 parts DEOA |
| 4.0 parts Water | 4.0 parts Water |
| 1.75 parts DC 5043 | 2.0 parts DC 5043 |
| 0.35 parts DABCO 33-LV | 0.12 parts DABCO 33-LV |
|  | 0.45 parts DABCO BL-17 |
| 0.12 parts DABCO BL-11 | 2.0 parts DtBMDCHA |

Cure conditions:
 Foams were prepared at an index of 100
 16"×16"×4" physical property mold
 6 minute cure at 140 F
 Foams aged at room temperature 5-7 days prior to testing
DEOA is diethanolamine, a common crosslinker.

DABCO BL-11 is a commercial catalyst of 70% bis(dimethylaminoethyl)ether, 30% dipropylene glycol.
DABCO BL-17 is BL-11 blocked with formic acid.
DABCO 33-LV catalyst is a 33% mixture of triethylenediamine in propylene glycol.
DC 5043 is a silicone surfactant.
Multranol 9143 is polyether triol (6000 mol wt) marketed by Mobay Co.
Multranol 9151 is a PHD polyol marketed by Mobay Co.

| Physical Property Comparison | | |
|---|---|---|
| Property | Control | DtBMDCHA-modified |
| Density (lb/cu ft) | 1.97 | 1.82 |
| IFD, 25% (lb) | 17.0 | 18.2 |
| IFD, 65% (lb) | 51.8 | 60.0 |
| Air Flow (cu ft/m) | 1.55 | 2.47 |
| Tear (lb/sq in) | 1.72 | 2.14 |
| Tensile (lb/sq in) | 15.1 | 17.3 |
| Elongation (%) | 89.5 | 109 |
| 50% Comp. Set | 17.4 | 9.31 |
| 50% HA Comp. Set | 31.8 | 26.1 |

At a level of 2.0 weight parts per 100 parts polyol (pph), the use of DtBMDCHA improved all of the measured mechanical or physical properties and concurrently reduced density. In addition, the DtBMDCHA-modified foams produced were relatively open celled, i.e., they required less crushing at demold than the control.

What is claimed is:

1. In a polyepoxide resin composition comprising a glycidyl ether of a polyhydric phenol, glycidyl polyester or glycidyl amine cured with an amine curing agent, the improvement which comprises utilizing as said curing agent, or component thereof, 3,3'ditertiarybutylmethylenedi(cyclohexylamine).

2. The polyepoxide resin of claim 2 wherein the polyepoxide resin is formed from a glycidyl ether of a polyhydric alcohol.

3. The polyepoxide resin of claim 3 wherein the glycidyl ether of a polyhydric alcohol is the reaction product of epichlorohydrin and 4,4'-(dihydroxydiphenyl)propane.

4. The polyepoxide resin of claim 3 wherein the molar equivalents of amine curing agent to polyepoxide resin is from 0.4 to 0.6:1.

5. The polyepoxide resin of claim 2 wherein the polyepoxide resin comprises a glycidyl amine and the glycidyl amine is a glycidyl derivative of methylenedianiline, paraaminophenol, or bis(paraaminocyclohexyl)methane.

6. A bridged di(cyclohexylamine) of the structure

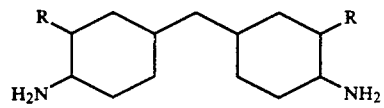

wherein R is tert-butyl.

* * * * *